US 6,724,924 B1

(12) United States Patent
Wei et al.

(10) Patent No.: US 6,724,924 B1
(45) Date of Patent: Apr. 20, 2004

(54) BRIGHTNESS AND CONTRAST INVARIANT DETECTION OF VERTEBRA PEDICLES

(75) Inventors: Guo-Qing Wei, Plainsboro, NJ (US); Jianzhong Qian, Princeton Jct., NJ (US); Helmuth Schramm, Neunkirchen (DE)

(73) Assignee: Siemens Corporate Research, Inc., Princeton, NJ (US)

( * ) Notice: Subject to any disclaimer, the term of this patent is extended or adjusted under 35 U.S.C. 154(b) by 566 days.

(21) Appl. No.: 09/638,121

(22) Filed: Aug. 14, 2000

(51) Int. Cl.$^7$ ................................................ G06K 9/00
(52) U.S. Cl. ...................................... 382/132; 382/190
(58) Field of Search ................................. 382/128, 132, 382/173, 190, 195, 278, 280; 128/922

(56) References Cited

U.S. PATENT DOCUMENTS 4,881,270 A * 11/1989 Knecht et al. ............... 382/191
5,943,435 A * 8/1999 Gaborski .................... 382/132
6,249,590 B1 * 6/2001 Young et al. ................ 382/103

OTHER PUBLICATIONS

Verdonck et al. "Computer Assisted Quantitive Analysis of Deformities of the Human Spine", Medical Image Computing and Computer–Assisted Intervention, Springer–Verlag, Proceedings of MICCAI '98, Cambridge, MA, Oct. 1998, pp. 822–831.*

Tascini et al., "Automatic Quantitative Analysis of Lumbar Bone Radiographs", Nuclear Science Symposium and Medical Imaging Conference, 1993 IEEE Conference Record, vol. 3 Oct. 31–Nov. 6, 1993, pp. 1722–1726.*

Kauffmann et al., "Digital Radiography Segmentation of Scoliotic Vertebral Body Using Deformable Models", Proc. SPIE vol. 3034: Medical Imaging 1997: Image Processing, Apr. 1997, pp. 243–251.*

* cited by examiner

Primary Examiner—Leo Boudreau
Assistant Examiner—Ryan J. Miller
(74) Attorney, Agent, or Firm—Donald B. Paschburg; F. Chau & Associates, LLP

(57) ABSTRACT

A system and method for detecting pedicle positions in an image, in accordance with the present invention, includes providing a set of feature prototypes for a plurality of pedicle positions and orientations, providing an input image to be analyzed for pedicle positions and orientations, and determining intensity curvatures for a pedicle in the input image. The intensity curvatures are transformed to determine a feature vector for the pedicle in the input image. The feature vector is correlated to the feature prototypes to determine most likely positions and orientations of the pedicle.

22 Claims, 3 Drawing Sheets

(a) A pedicle image (b) The curvature extreme

BRIGHTNESS AND CONTRAST INVARIANT DETECTION OF VERTEBRA PEDICLES

BACKGROUND

1. Technical Field

This disclosure relates to radiographic imaging and detection, and more particularly, to a method for automatically detecting and measuring pedicles in spine images.

2. Description of the Related Art

In the radiographic diagnosis of spines, pedicles are an important anatomy for measuring rotational deformity. Pedicles may vary significantly in position, size, and shape, and may also appear in images with different brightness and contrast. These variations are rich in diagnostic information. Computer detection, measurement, and characterization of pedicles and their variations provide efficient and accurate ways in clinical diagnostic practice, yet pose substantial difficulties and challenges to the development of automatic computerized methods.

Currently, detection, measurement, and characterization of pedicles is performed manually by physicians, and is therefore subject to human errors and usually is not reproducible.

Therefore, a need exists to provide a method for automatic pedicle detection and measurement. A further need exists for a method, which is immune from changes in image brightness and image contrast.

SUMMARY OF THE INVENTION

A method for detecting pedicle positions in an image, preferably a radiographic image, in accordance with the present invention, includes providing a set of feature prototypes for a plurality of pedicle positions and orientations, providing an input image to be analyzed for pedicle positions and orientations, and determining intensity curvatures for a pedicle in the input image. The intensity curvatures are transformed to determine a feature vector for the pedicle in the input image. The feature vector is correlated to the feature prototypes to determine most likely positions and orientations of the pedicle.

Another method for detecting pedicle positions in an image of a spine, includes the step of training a set of feature prototypes for a plurality of pedicle positions and orientations. The training step is performed by selecting images of pedicles in different positions and orientations, determining intensity curvatures of the images, transforming the intensity curvatures to determine features for the pedicles for each training sample, and performing an eigenvalue decomposition to provide a set of feature prototypes. An input image is provided to be analyzed for pedicle positions and orientations, and pedicle locations and orientations are detected. The pedicle locations and orientations are detected by determining intensity curvatures for the input image of the pedicle in the input image, transforming the intensity curvatures to determine a feature vector for the pedicle in the input image and correlating the feature vector to the feature prototypes to determine most likely positions and orientations of the pedicle.

In other methods, the bone preferably includes a pedicle, but other specialized bones may be determined in accordance with the invention. The step of providing a set of feature prototypes may include the steps of selecting images of the pedicle in different positions and orientations, determining intensity curvatures of the images, transforming the intensity curvatures to determine features for the pedicle for each orientation and position and performing an eigenvalue decomposition to provide the set of feature prototypes. The step of transforming the intensity curvatures to determine features for the pedicle for each orientation and position may include employing one of a discrete cosine transformation and a wavelet transformation. The step of transforming the intensity curvatures to determine a feature vector for the pedicle in the input image may include employing one of a discrete cosine transformation and a wavelet transformation.

In still other methods, the step of correlating the feature vector to the feature prototypes to determine most likely positions and orientations of the pedicle may include the steps of projecting the feature vector to the feature prototypes to create a reconstructed feature set, and comparing the reconstructed feature set to the feature vector to determine the most likely positions and orientations of the pedicle. The method may include the step of repeating the comparing step for a plurality of different image resolutions. The method may further include the step of marking position points on the input image. The above methods may be implemented by a program storage device readable by machine, tangibly embodying a program of instructions executable by the machine to perform these method steps.

These and other objects, features and advantages of the present invention will become apparent from the following detailed description of illustrative embodiments thereof, which is to be read in connection with the accompanying drawings.

BRIEF DESCRIPTION OF DRAWINGS

This disclosure will present in detail the following description of preferred embodiments with reference to the following figures wherein.

DETAILED DESCRIPTION OF PREFERRED EMBODIMENTS

The present invention provides methods for automatic pedicle detection and measurement. The present invention is capable of dealing with changes in image brightness and image contrast, so that the pedicle detection is made immune to such changes. Also, the present invention handles variations in pedicle shapes. Shape variations will not deteriorate the performance of the detection by using the techniques of the present invention. The present invention, therefore, provides stable and robust detection of pedicles and the provision of quantitative and accurate measurement information for the characterization of different abnormalities or diseases of the spine of a patient.

In particularly useful embodiments, the present invention presents an automatic method for pedicle detection and measuring in spine X-ray images. The detection accuracy is not influenced by changes of image brightness and image contrast. Variations in pedicle shapes are learned by a training-based method. Data compression techniques are used to both reduce the data dimension for a fast training and detection and to enable a multi-scale search without multi-scale training. The detected pedicles can be used for automatic measurements and characterization of spine related ailments or analysis.

Although this disclosure employs the illustrative example of pedicle analysis, the methods and system described herein may be employed for tracking and defining other anatomical features, structures or organs. For example, the detection method of the present invention may be employed for planning surgical procedures for setting fractured or broken bones or identifying special bone structures.

Figure 1:
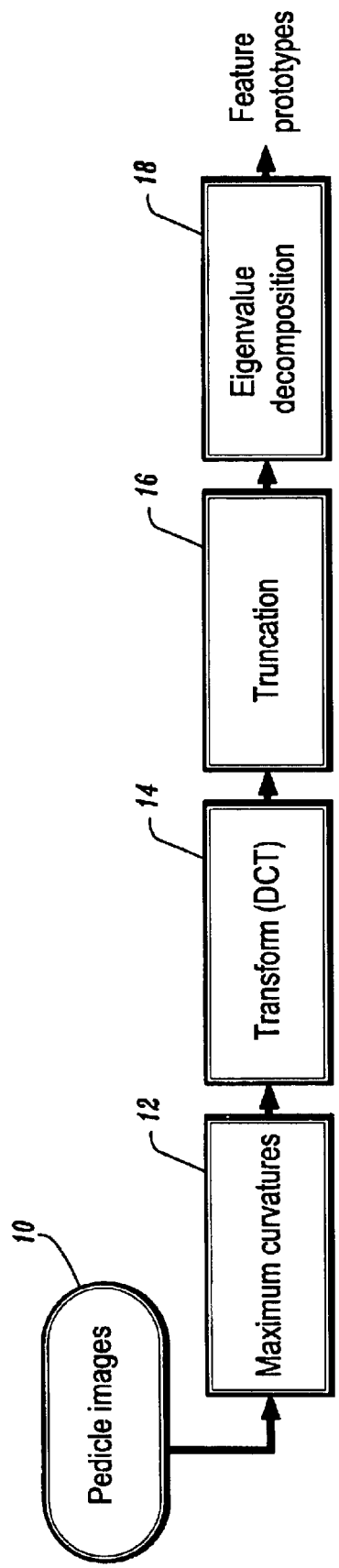
FIG. 1 is a block/flow diagram showing a training phase for providing feature prototypes of pedicles in accordance with the present invention.
Figure 2:
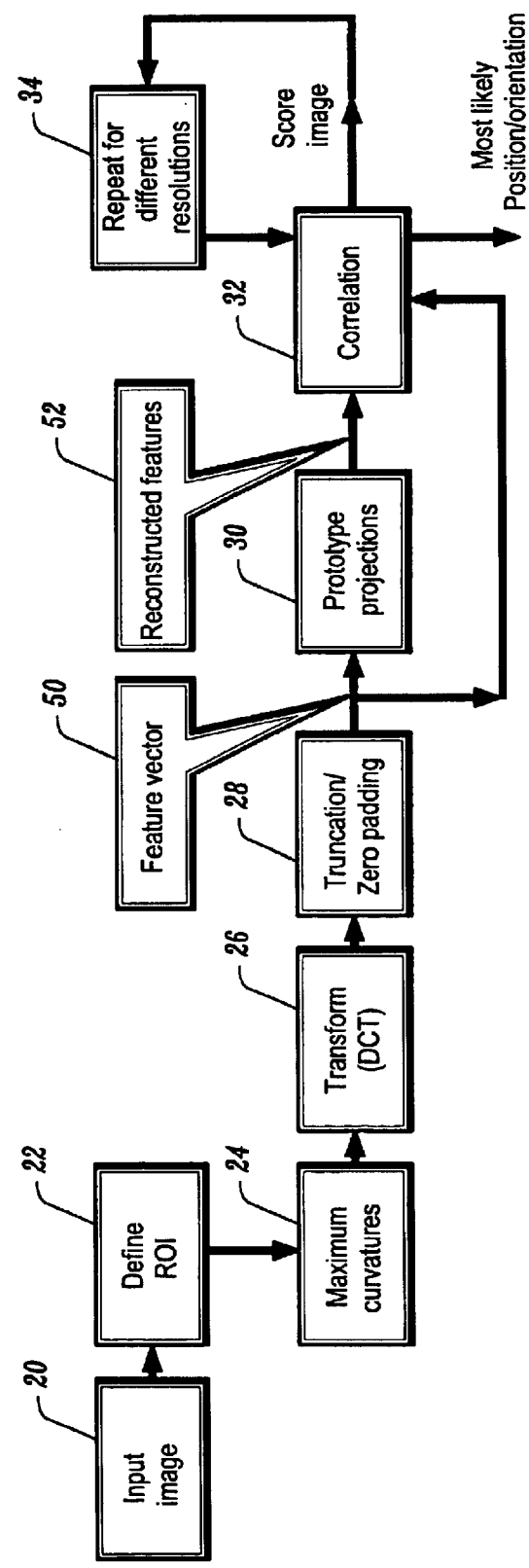
FIG. 2 is a block/flow diagram showing a detection phase for detecting pedicles and determining position and orientations of the pedicles in accordance with the present invention.

It should be understood that the elements shown in FIGS. 1 and 2 may be implemented in various forms of hardware, software or combinations thereof. Preferably, these elements are implemented on one or more appropriately programmed general purpose digital computers having a processor and memory and input/output interfaces.

Referring now in specific detail to the drawings in which like reference numerals identify similar or identical elements throughout the several views, and initially to FIGS. 1 and 2, a pedicle detection method and system includes two phases: a training phase (FIG. 1) and a detection phase (FIG. 2). In block 10 of the training phase, a set of images, such as spine images, are selected and normalized to a particular size, which is automatically adapted to the spine width of each image. Then, pedicle images of typical pedicle shapes are collected to form a set of training data. Each pedicle image in the training set has the same size and includes only one pedicle. The image of a spine is preferably taken by X-ray, although other imaging technologies may be employed, such as computerized axial tomography (e.g., CAT scan), sonogram, magnetic resonance (MRI) or other techniques. The image is preferably converted or taken in digital form.

Two sequential transformations are then applied to each pedicle image in the training set. As a first transformation, in block 12, intensity curvatures of maximum absolute values are computed at each image point. This gives a brightness invariant representation and enhances the pedicle boundaries. The ridge map computation is based on the second order derivatives of the intensity image in the horizontal, vertical and/or diagonal directions. The direction value of the ridge map at a pixel is the maximum (extreme) curvature of the intensity profiles across that pixel in all directions. The direction which the curvature achieves the maximum is recorded for each pixel. This forms the orientation map. For example, suppose there is a white line in a dark background. For pixels one the white line, the curvature achieves a maximum in the direction orthogonal to the line orientation. The value of the maximum curvature is the value in the curvature extreme map and the orientation (orthogonal to the line) is the value in the orientation map.

Figure 3:
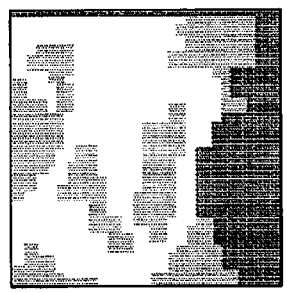
FIG. 3 depicts an image of a pedicle to be analyzed in accordance with the present invention.
Figure 4:
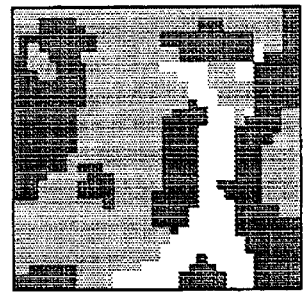
FIG. 4 depicts an image of the pedicle of FIG. 3 after being processed for curvature extremes in accordance with the present invention.

Any brightness shift, e.g., by adding a constant to the image intensity, will not affect the intensity curvatures, which is a measure of how fast intensity changes from point to point in the image. Referring to FIGS. 3 and 4, a pedicle image (FIG. 3) is shown with its curvature extreme representation (FIG. 4). As shown in FIG. 4, bright pixels represent positive curvatures, and dark pixels represent negative curvatures.

As a second transformation, in block 14, the curvature images are then compressed by applying the Discrete Cosine Transform (DCT) or other image compression methods, such as, for example, a Wavelet Transform. Suppose $x(n_1, n_2)$ is the curvature image. Then the DCT transformation of $x(n_1, n_2)$ is $$X[k_1, k_2] = \alpha[k_1]\alpha[k_2]\sum_{n_1=0}^{N-1}\sum_{n_2=0}^{N-1} x[n_1, n_2]\cos\left(\frac{\pi(2n_1+1)k_1}{2N}\right)\cos\left(\frac{\pi(2n_2+1)k_2}{2N}\right)$$

$$k_1, k_2 = 0, 1, \ldots, N-1$$

and $$\alpha[k] = \begin{cases} \sqrt{\frac{1}{N}} & \text{for } k = 0 \\ \sqrt{\frac{2}{N}} & \text{for } k = 1, 2, \ldots, N-1 \end{cases}$$

where N is the dimension of $x(n_1, n_2)$.

Figure 5:
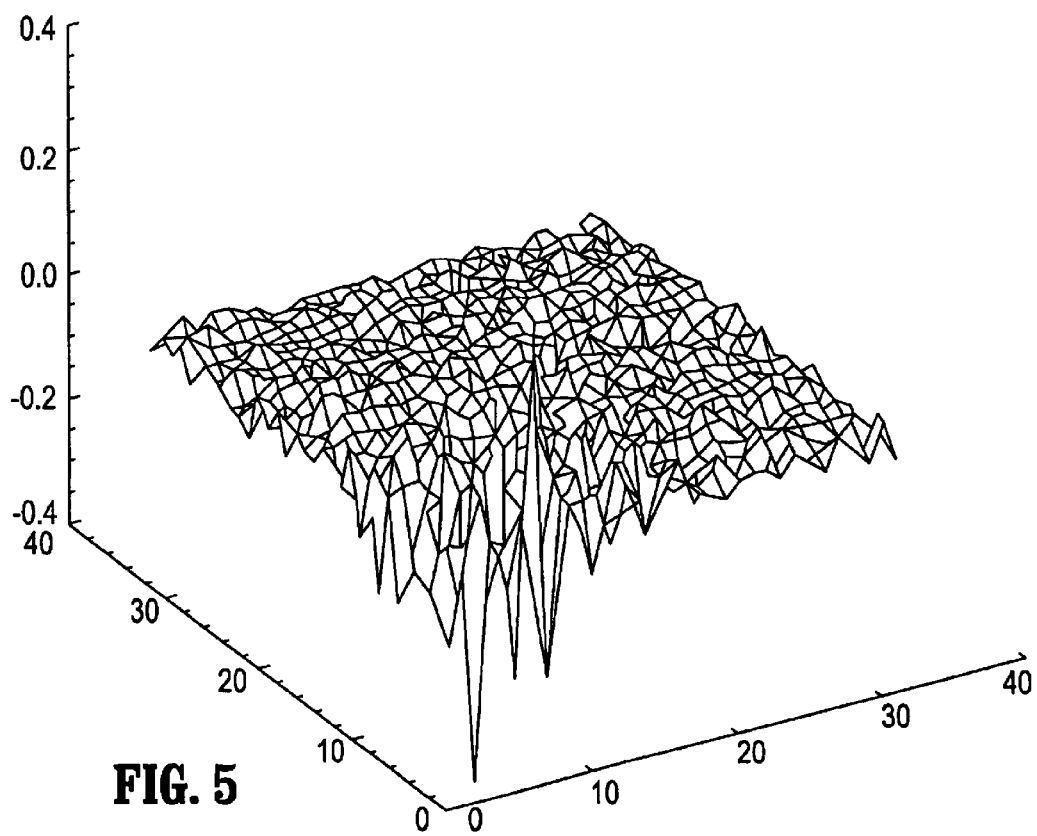
FIG. 5 is a plot showing the results of a discrete cosine transformation of the image of FIG. 4 in accordance with the present invention.

Referring to FIG. 5, a surface plot of the DCT transformation of FIG. 4 is shown, where the coordinate origin is at the lowest corner of the image, the two slanted axes represent $k_1$ and $k_2$, and the vertical axis represents X. Compression is achieved by keeping a portion, say $k_1 \times k_2 = [0, k_{1\,max}] \times [0, k_{2\,max}]$, around the corner $(k_1, k_2) = (0,0)$ of the DCT transformation. Because X values outside that region are very small and can be neglected.

In block 16, a truncation operation reduces the number of dimensions of pedicle feature vectors. Blocks 14 and 16 are optional although preferred, since the DCT and the resulting truncation of block 16 provides a computationally less expensive decomposition step to form feature prototypes or models. In one implementation of the present invention, the truncations for $k_1$ and $k_2$ are preferably made and half of the image dimension N, e.g., $k_{1\,max} = N/2$, $k_{2\,max} = N/2$. In the full resolution, the DCT transform has a dimension of N×N, whereas the truncation reduces this to N×N/4.

In block 18, the pedicle features from block 16 are subsequently analyzed to find the prototype features preferably by eigenvalue decomposition. Eigenvalue decomposition may be performed by standard techniques known to those skilled in the art of numerical analysis in mathematics. Prototype features are the remembered or stored pedicle features used in the detection phase. The dimension reduction by DCT permits the eigenvalue decomposition to be performed much faster than if the original curvature feature of block 12 were employed to manufacture the feature models or prototypes. The feature prototypes may include images or feature vectors describing the pedicle images of block 10.

As shown in FIG. 2, in block 20 of the detection phase, an image to be evaluated is input to the system. In a preferred embodiment, the image is a digitized X-ray image although other image technologies may be employed. In block 22, a region-of-interest (ROI) in the input image is defined by anatomic landmarks, such as, for example, endplates and spine boundaries. This is preferably performed by multi-scale approaches, in which a procedure is applied to images of different resolution (scales) beginning form the coarsest resolution and moving into finer resolutions. The image needs to be downsized to different resolutions of a specified number. In one implementation of the present invention, the number of resolutions is 2.

In block 24, feature selection is performed in the same way as described for block 12 above. In block 26, transformations, such as DCT, are carried out in the same way as in block 14 of the training phase. In block 28, depending on the size of the downsized image, the features are either truncated or zero-padded to the same dimension as in the training phase. Truncation may include going from an N×N dimension vector to a $k_{1\ max} \times k_{2\ max}$ dimension vector. Zero-padding is performed for resolutions, in which downsizing of N×N gives a smaller dimension than $k_{1\ max} \times k_{2\ max}$, say $k_{1\ min} \times k_{2\ min}$, where $k_{1\ min} < k_{1\ max}$ and $k_{2\ min} < k_{2\ max}$. The region represented by $k_{1\ min} \times k_{2\ min}$ needs to be zero-padded or adjusted to a region of size $k_{1\ max} \times k_{2\ max}$.

In block 30, features 50 at each current pixel are projected to the prototype features (from FIG. 1) and the projections are combined to form a reconstructed feature set 52. Suppose f is the current feature vector, and F={$f_i$, i=0,1, . . . M} is the set of prototype feature vectors, where $f_0$ is the mean (or average) feature vector, and M is the number of prototype feature vectors. The projection of the current feature vector onto the prototype features is made by the following:

$$\tilde{f} = f_0 + \sum_{i=1}^{M} \alpha_i f_i$$

with $$\alpha_i = (f - f_0) \cdot f_i$$

where $\forall_i$ is the projection of f onto $f_i$ (the symbol * represents the dot product operation of two vectors).

The two feature sets f and $\tilde{f}$ are then compared in block 32 to find the degree of correlation.

In block 32, contrast invariance is achieved with the correlation measure or image score. Positions of the M largest correlation values (e.g., most likely matches) are carried over to the next image resolution as candidate positions. At the next image resolution, only candidate positions are tested. The same is repeated, in block 34, until the finest resolution is reached, in which the position with the maximum score is picked as the position of the detected pedicle. Advantageously, with the DCT data compression, the same feature prototypes can be used across all image resolutions without the need to re-train the system at each resolution.

Figure 6:
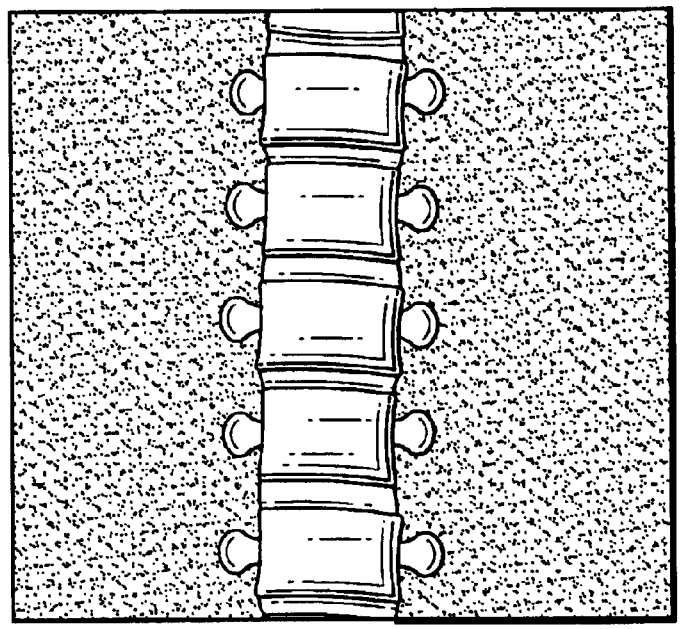
FIG. 6 depicts an image of a spine to be analyzed for pedicle position and orientation in accordance with the present invention.

Referring to FIG. 6, an image of a spine is shown to be employed for pedicle detection in accordance with the present invention. The present invention is applied to the image to detect and analyze the position of pedicles in the spine image.

Figure 7:
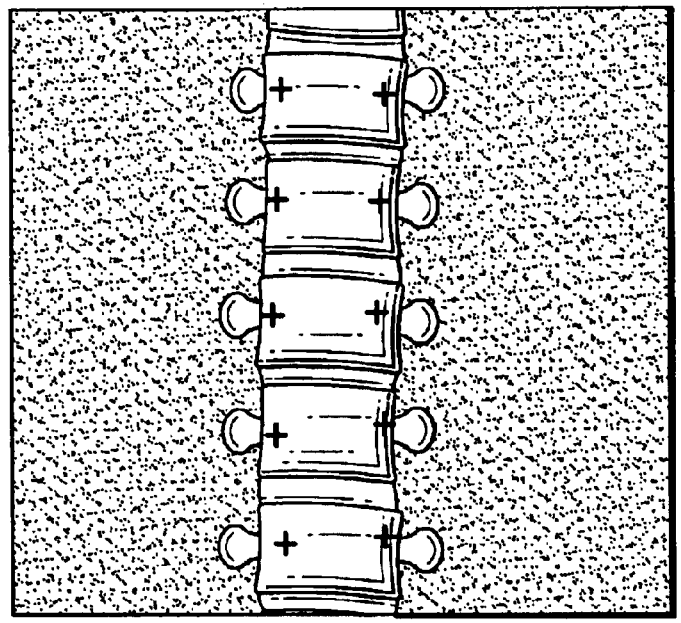
FIG. 7 depicts the image of FIG. 6 where keys points of the pedicles have been marked with crosses in accordance with the present invention.

Referring to FIG. 7, after the completion of automatic detection of pedicles, the computer automatically detects several key points on the detected pedicles. Key points in this example are shown as crosses designating center portions of pedicles in the spine image of FIG. 6. These key points then are used to perform measurements, such as the relative position or distance of a pair of pedicles, the degree of rotation or twists of the pair of pedicles. These measurements may employed to characterize different abnormalities or diseases of the spine of the patient. For example, the position of the detected pedicles with respect to the vertebra axis is used as the basis for determination of the rotational component of scoliosis according to the Nash and Moe method, which is known to those skilled in the art. The disease classification based on the measurement data is preferably performed by physicians.

Having described preferred embodiments for brightness and contrast invariant detection of vertebra pedicles (which are intended to be illustrative and not limiting), it is noted that modifications and variations can be made by persons skilled in the art in light of the above teachings. It is therefore to be understood that changes may be made in the particular embodiments of the invention disclosed which are within the scope and spirit of the invention as outlined by the appended claims. Having thus described the invention with the details and particularity required by the patent laws, what is claimed and desired protected by Letters Patent is set forth in the appended claims.

What is claimed is:

1. A method for detecting pedicle positions in an image, comprising the steps of:
    providing a set of feature prototypes for a plurality of pedicle positions and orientations;
    providing an input image to be analyzed for pedicle positions and orientations;
    determining intensity curvatures for a pedicle in the input image;
    transforming the intensity curvatures to determine a feature vector for the pedicle in the input image; and
    correlating the feature vector to the feature prototypes to determine most likely positions and orientations of the pedicle.

2. The method as recited in claim 1, wherein the image includes an X-ray image.

3. The method as recited in claim 1, wherein the step of providing a set of feature prototypes includes the steps of:
    selecting images of the pedicle in different positions and orientations;
    determining intensity curvatures of the images;
    transforming the intensity curvatures to determine features for the pedicle for each orientation and position; and
    performing an eigenvalue decomposition to provide the set of feature prototypes.

4. The method as recited in claim 3, wherein the step of transforming the intensity curvatures to determine features for the pedicle for each orientation and position includes employing one of a discrete cosine transformation and a wavelet transformation.

5. The method as recited in claim 1, wherein the step of transforming the intensity curvatures to determine a feature vector for the pedicle in the input image includes employing one of a discrete cosine transformation and a wavelet transformation.

6. The method as recited in claim 1, wherein the step of correlating the feature vector to the feature prototypes to determine most likely positions and orientations of the pedicle includes the steps of:
    projecting the feature vector to the feature prototypes to create a reconstructed feature set; and
    comparing the reconstructed feature set to the feature vector to determine the most likely positions and orientations of the pedicle.

7. The method as recited in claim 6, further comprising the step of repeating the comparing step for a plurality of different image resolutions.

8. The method as recited in claim 1, further comprising the step of marking position points on the input image.

9. A method for detecting pedicle positions in an image of a spine, comprising the steps of:
   training a set of feature prototypes for a plurality of pedicle positions and orientations by:
      selecting images of pedicles in different positions and orientations;
      determining intensity curvatures of the images;
      transforming the intensity curvatures to determine features for the pedicles for each orientation and position; and
      performing an eigenvalue decomposition to provide a set of feature prototypes;
   providing an input image to be analyzed for pedicle positions and orientations; and
   detecting pedicle locations and orientations by:
      determining intensity curvatures for the input image of the pedicle in the input image;
      transforming the intensity curvatures to determine a feature vector for the pedicle in the input image; and
      correlating the feature vector to the feature prototypes to determine most likely positions and orientations of the pedicle.

10. The method as recited in claim 9, wherein the step of transforming the intensity curvatures to determine features for the pedicles for each orientation and position includes employing one of a discrete cosine transformation and a wavelet transformation.

11. The method as recited in claim 9, wherein the step of transforming the intensity curvatures to determine a feature vector for the pedicle in the input image includes employing one of a discrete cosine transformation and a wavelet transformation.

12. The method as recited in claim 9, wherein the step of correlating the feature vector to the feature prototypes to determine most likely positions and orientations of the pedicle includes the steps of:
   projecting the feature vector to the feature prototypes to create a reconstructed feature set; and
   comparing the reconstructed feature set to the feature vector to determine the most likely positions and orientations of the pedicle.

13. The method as recited in claim 12, further comprising the step of repeating the comparing step for a plurality of different image resolutions.

14. The method as recited in claim 9, further comprising the step of marking position points on the input image.

15. A program storage device readable by machine, tangibly embodying a program of instructions executable by the machine to perform method steps for detecting pedicle positions in an image, the method steps comprising:
   providing a set of feature prototypes for a plurality of pedicle positions and orientations;
   providing an input image to be analyzed for pedicle positions and orientations;
   determining intensity curvatures for a pedicle in the input image;
   transforming the intensity curvatures to determine a feature vector for the pedicle in the input image; and
   correlating the feature vector to the feature prototypes to determine most likely positions and orientations of the pedicle.

16. The program storage device as recited in claim 15, wherein the image includes a digital X-ray image.

17. The program storage device as recited in claim 15, wherein the step of providing a set of feature prototypes includes the steps of:
   selecting images of the pedicle in different positions and orientations;
   determining intensity curvatures of the images;
   transforming the intensity curvatures to determine features for the pedicle for each orientation and position; and
   performing an eigenvalue decomposition to provide the set of feature prototypes.

18. The program storage device as recited in claim 17, wherein the step of transforming the intensity curvatures to determine features for the pedicle for each orientation and position includes employing one of a discrete cosine transformation and a wavelet transformation.

19. The method as recited in claim 15, wherein the step of transforming the intensity curvatures to determine a feature vector for the pedicle in the input image includes employing one of a discrete cosine transformation and a wavelet transformation.

20. The program storage device as recited in claim 15, wherein the step of correlating the feature vector to the feature prototypes to determine most likely positions and orientations of the pedicle includes the steps of:
   projecting the feature vector to the feature prototypes to create a reconstructed feature set;
   comparing the reconstructed feature set to the feature vector to determine the most likely positions and orientations of the pedicle.

21. The program storage device as recited in claim 20, further comprising the step of repeating the comparing step for a plurality of different image resolutions.

22. The program storage device as recited in claim 15, further comprising the step of marking position points on the input image.

* * * * *